United States Patent
Choi et al.

(10) Patent No.: US 7,666,446 B2
(45) Date of Patent: Feb. 23, 2010

(54) ORAL FORMULATION FOR DELIVERY OF POORLY ABSORBED DRUGS

(75) Inventors: Seung-Ho Choi, Salt Lake City, UT (US); Seong-Wan Cho, Jeonju (KR)

(73) Assignee: ProCarrier, Inc., Park City, UT (US)

( * ) Notice: Subject to any disclaimer, the term of this patent is extended or adjusted under 35 U.S.C. 154(b) by 718 days.

(21) Appl. No.: 10/973,644

(22) Filed: Oct. 25, 2004

(65) Prior Publication Data

US 2006/0088592 A1 Apr. 27, 2006

(30) Foreign Application Priority Data

Apr. 28, 2004 (KR) .................... 10-2004-0029465

(51) Int. Cl.
 A61K 6/14 (2006.01)
 A61K 9/16 (2006.01)
 A61K 9/20 (2006.01)
 A61K 9/28 (2006.01)
 A61K 9/48 (2006.01)

(52) U.S. Cl. .................. 424/464; 424/451; 424/452; 424/463; 424/645; 424/474; 424/489; 424/490

(58) Field of Classification Search .................. None
See application file for complete search history.

(56) References Cited

U.S. PATENT DOCUMENTS

| | | | |
|---|---|---|---|
| 5,690,954 A | 11/1997 | Illum | |
| 5,731,006 A * | 3/1998 | Akiyama et al. | 424/502 |
| 6,017,545 A | 1/2000 | Modi | |
| 6,258,848 B1 * | 7/2001 | Fantus | 514/562 |
| 6,309,663 B1 * | 10/2001 | Patel et al. | 424/450 |
| 6,420,350 B1 * | 7/2002 | Fleischner | 514/62 |
| 6,432,383 B1 | 8/2002 | Modi | |
| 6,517,860 B1 | 2/2003 | Roser et al. | |
| 6,638,534 B1 | 10/2003 | Ishibashi et al. | |
| 6,734,170 B2 | 5/2004 | Petit, II et al. | |
| 2001/0018072 A1 | 8/2001 | Unger | |

(Continued)

FOREIGN PATENT DOCUMENTS

JP 56140924 A * 11/1981

(Continued)

OTHER PUBLICATIONS

Chitosan. Wikipedia.com. Acessed online on Jun. 8, 2007. <http://en.wikipendia.org/wiki/Chitosan>.*

(Continued)

*Primary Examiner*—S. Tran
(74) *Attorney, Agent, or Firm*—Clayton, Howarth & Cannon, P.C.

(57) ABSTRACT

A composition for oral delivery of a poorly absorbed drug is disclosed. The composition includes the drug, an enhancer for increasing absorption of the drug through the intestinal mucosa, a promoter, which alone does not increase absorption of the drug through the intestinal mucosa, but which further increases the absorption of the drug in the presence of the enhancer, and optionally a protector for protecting the drug from physical or chemical decomposition or inactivation in the gastrointestinal tract. Illustrative enhancers include sucrose fatty acid esters, and illustrative promoters include aminosugars and amino acid derivatives, such as poly(amino acids). Illustrative protectors include methylcellulose, poly(vinyl alcohol), and poly(vinyl pyrrolidone).

21 Claims, 4 Drawing Sheets

U.S. PATENT DOCUMENTS

| | | |
|---|---|---|
| 2002/0009491 A1 | 1/2002 | Rothbard et al. |
| 2002/0044972 A1 | 4/2002 | Davis et al. |
| 2002/0058714 A1 | 5/2002 | Maruyama |
| 2003/0064934 A1 | 4/2003 | Naito |
| 2003/0091640 A1 | 5/2003 | Ramanathan et al. |
| 2003/0124196 A1* | 7/2003 | Weinbach et al. ........... 424/499 |
| 2003/0147962 A1 | 8/2003 | Bernstein et al. |
| 2003/0170309 A1 | 9/2003 | Babcock et al. |
| 2003/0190364 A1 | 10/2003 | Panitch et al. |
| 2003/0195179 A1 | 10/2003 | Sawa |
| 2003/0211072 A1 | 11/2003 | Carreno-Gomez et al. |
| 2003/0219489 A1 | 11/2003 | Curatolo et al. |
| 2004/0076675 A1 | 4/2004 | Sugishita et al. |
| 2004/0167203 A1 | 8/2004 | Chang et al. |
| 2004/0171581 A1 | 9/2004 | Rastrelli et al. |

FOREIGN PATENT DOCUMENTS

| | | |
|---|---|---|
| WO | 9706813 A1 | 2/1997 |
| WO | WO 9706813 A1 * | 2/1997 |

OTHER PUBLICATIONS

"Citric Acid". Handbook of Pharmaceutical Excipients. 1986. pages 78-80.*

Seong Wan Cho et al., "Enhanced Oral Absorption of insulin delivered in the ProCarrier® system," Third Annual Diabetes Technology Meeting, Nov. 6-8, 2003, San Francisco.

Seong Wan Cho et al., "Enhanced oral bioavailability of Recombinant Human Growth Hormone (rhGH)," 2003 AAPS Annual Meeting and Exposition, Oct. 26-30, 2003, Salt Lake City.

* cited by examiner

ORAL FORMULATION FOR DELIVERY OF POORLY ABSORBED DRUGS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to drug delivery. More particularly, this invention relates to compositions and methods for oral delivery of poorly absorbed drugs.

The gastrointestinal tract, particularly the small intestines, is the primary site for absorption of nutrients and most bioactive agents. To accommodate the processes of absorption, the amount of surface area in the small intestines is enlarged due to the presence of villi and microvilli. However, before a bioactive compound is transferred from the intestinal lumen to the blood, the compound may be subject to degradation or deactivation by the various components of the lumen. Moreover, the compound may be required to pass through several barriers to absorption, such as the mucous layer and the intestinal brush-border membrane. Many compounds pass these barriers easily, but there are many nutrients and bioactive agents to which these barriers represent a serious obstruction.

There are many factors that can affect the oral bioavailability of drugs in the gastrointestinal tract. They include, for example, factors relating to the drug itself, such as active or passive transport, water solubility, molecular weight, chemical stability, ionization, pH, and the like; factors relating to chemical processes, such as deamination, hydrolysis (or ionization), oxidation, racemization, beta elimination, disulfide exchange, and the like; and factors relating to physical processes, such as aggregation, precipitation, denaturation, adsorption, and the like.

While prior art products and methods of use thereof are known and are generally suitable for their limited purposes, they possess certain inherent deficiencies that detract from their overall utility in delivering poorly absorbable drugs by the oral route. Namely, these prior art products and processes fail to increase intestinal absorption of the drugs while preventing physical and/or chemical decomposition or inactivation of the drugs.

In view of the foregoing, it will be appreciated that providing compositions and methods for efficient oral delivery of poorly absorbed drugs would be a significant advancement in the art.

BRIEF SUMMARY OF THE INVENTION

It is a feature of illustrative embodiments of the present invention to provide compositions and methods of use and making thereof that enhance intestinal absorption of drugs delivered by the oral route and simultaneously reduce or inhibit decomposition or inactivation of the drugs due to physical and/or chemical factors.

These and other objects can be addressed by providing a composition for oral delivery of a pharmaceutical agent that is poorly absorbed through the intestinal mucosa, the composition comprising a mixture of an effective amount of the pharmaceutical agent; an enhancer for increasing absorption of the pharmaceutical agent through the intestinal mucosa; a promoter that functions synergistically with the enhancer for further increasing absorption of the pharmaceutical agent through the intestinal mucosa; and optionally a protector for inhibiting decomposition or inactivation of the pharmaceutical agent;

wherein the enhancer is a member selected from the group consisting of fatty acid esters, phospholipids, phosphatidyl compounds, glycosylceramides, fatty acids, nonionic surfactants, vitamin E tocopheryl succinate polyethylene glycol, glycerides, derivatives thereof, and mixtures thereof;

wherein the promoter is a member selected from the group consisting of amino acid derivatives, aminosugars, and mixtures thereof; and wherein the protector is a member selected from the group consisting of carbomers, carboxymethylcellulose, polysaccharides, pectin, cellulose, dextrin, gelatin, polyethylene oxide, poly(vinyl alcohol), poly(vinyl propylene), poly(vinylpyrrolidone), xanthan gums, sodium alginate, methacrylic acid copolymers, colloidal silica, synthetic silica, polysaccharides, water-soluble cellulose ethers, hydroxypropylmethacrylates, tragacanth, water-soluble chitosan, polycarbophil, derivatives thereof, and mixtures thereof.

Another illustrative embodiment of the invention comprises a composition for oral delivery of a pharmaceutical agent that is poorly absorbed through the intestinal mucosa after oral administration, the composition comprising a mixture of an effective amount of the pharmaceutical agent; an enhancer for increasing absorption of the pharmaceutical agent through the intestinal mucosa wherein the enhancer comprises a sucrose fatty acid ester; a promoter that functions synergistically with the enhancer for increasing absorption of the pharmaceutical agent through the intestinal mucosa when wherein the promoter comprises glucosamine or poly(L-lysine); and optionally a protector for inhibiting decomposition or inactivation of the pharmaceutical agent wherein the protector comprises methylcellulose or poly(vinyl alcohol).

Still another illustrative embodiment of the invention comprises a composition for oral delivery of a hydrophilic or amphipathic drug, the composition comprising a mixture of the drug and an enhancer for increasing absorption of the drug through the intestinal mucosa, wherein the enhancer is a member selected from the group consisting of fatty acid esters, phospholipids, phosphatidyl compounds, glycosylceramides, fatty acids, nonionic surfactants, vitamin E tocopheryl succinate polyethylene glycol, glycerides, derivatives thereof, and mixtures thereof; and a promoter for functioning synergistically with the enhancer for further increasing absorption of the drug through the intestinal mucosa, wherein the promoter is a member selected from the group consisting of poly(amino acids), aminosugars, and mixtures thereof.

Yet another illustrative embodiment of the invention comprises a dosage form for oral delivery of a drug that is poorly absorbable in the intestine, the dosage form comprising an effective amount of the drug;

an enhancer for increasing absorption of the drug through the intestinal mucosa;

a promoter for functioning synergistically with the enhancer for further increasing absorption of the drug through the intestinal mucosa; and optionally, a protector for reducing or inhibiting decomposition or inactivation of the drug in the gastrointestinal tract.

A still further illustrative embodiment of the invention comprises a method for increasing intestinal absorption of a poorly absorbable drug, the method comprising orally administering a composition comprising a mixture of the drug;

an enhancer for increasing absorption of the drug through the intestinal mucosa;

a promoter that functions synergistically with the enhancer for further increasing absorption of the drug through the intestinal mucosa; and optionally, a protector for reducing or inhibiting decomposition or inactivation of the drug in the gastrointestinal tract.

DETAILED DESCRIPTION

Figure 1:
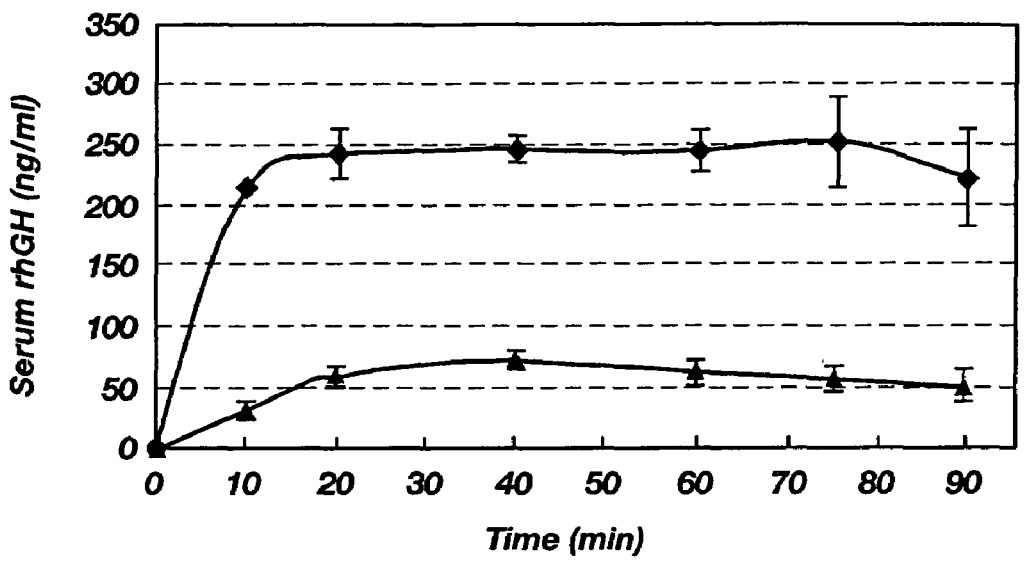
FIG. 1 shows serum recombinant human growth hormone (rhGH) concentration over time after subcutaneous injection with 0.1 mg/kg rhGH (▲) or 0.5 mg/kg rhGH (♦).

Before the present compositions and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to an oral drug-containing composition containing "a drug" includes a mixture of two or more of such drugs, reference to "an enhancer" includes reference to one or more of such enhancers, and reference to "a protector" includes reference to a mixture of two or more of such protectors.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of." As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

As used herein, "protector" means a biopolymer that serves to protect the drug from decomposition or inactivation due to the conditions encountered in the small intestines. The protector does not form a complex with the drug and is not covalently bonded to the drug. Exemplary protectors according to the present invention include methylcellulose, hydroxypropyl cellulose, polyvinyl pyrrolidone (PVP), polyvinyl alcohol (PVA), and mixtures thereof.

As used herein, "enhancer" means a substance that enhances or increases the absorption of a drug or other pharmaceutical agent across the intestinal mucosa after delivery of the drug or pharmaceutical agent by the oral route. Illustrative enhancers include surfactants, such as sucrose esters, and the like.

As used herein, "promoter" means a substance that exhibits little or no effect for enhancing or increasing the absorption of a drug or other pharmaceutical agent across the intestinal mucosa after delivery of the drug or pharmaceutical agent by the oral route, but that increases the absorption enhancing effect of an enhancer when the drug or pharmaceutical agent is delivered in combination with or together with an enhancer and a promoter. Thus, for example, oral administration of a composition comprising a mixture of a drug or other pharmaceutical agent, an enhancer, and a promoter results in greater absorption of the drug or pharmaceutical agent through the intestinal mucosa than does oral administration of a similar composition that lacks the promoter. Illustrative promoters include aminosugars and amino acid derivatives, such as poly (amino acids).

As used herein, "derivative" means a modified version of a compound or molecule. For example, such modified version may include, without limitation, a polymer, copolymer, ester, alkylated version, arylated version, aralkylated version, or the like of the compound or molecule.

As used herein, "surfactant" or "surface active agent" means a substance that alters energy relationships at interfaces, such as, for example, synthetic organic compounds displaying surface activity, including, among others, wetting agents, detergents, penetrants, spreaders, dispersing agents, and foaming agents. Illustrative examples of surfactants useful in the present invention are nonionic surfactants.

As used herein, "HLB" means "hydrophilic-lipophilic balance," which is an empirical quantity, on an arbitrary scale, that is a measure of the polarity of a surfactant or mixture of surfactants. P. Becher et al, Nonionic Surfactant Physical Chemistry 439-56 (Marcel Dekker, NY 1987). It is a widely known and used term. See, e.g., U.S. Pat. No. 5,707,648.

As used herein, "effective amount" means an amount of a drug or pharmacologically active agent that is nontoxic but sufficient to provide the desired local or systemic effect and performance at a reasonable benefit/risk ratio attending any medical treatment.

As used herein, "peptide" means peptides of any length and includes oligopeptides, polypeptides, and proteins. The only limitation to the peptide or protein drug that may be used according to the present invention is functionality.

As used herein, "poorly absorbed drug" and similar terms mean drugs or other pharmacologically active agents that are not readily absorbed through the intestinal mucosa into the bloodstream after oral administration, such that such drugs or pharmaceutical agents are not ordinarily administered by the oral route. In other words, "poorly absorbed drugs" include drugs that are normally administered by injection or transdermal or transmucosal administration because of poor absorption into the bloodstream after oral administration or decomposition or inactivation due to physical and/or chemical factors, as described above. Illustrative of poorly absorbed drugs are peptide or protein drugs, aminoglycoside antibiotics, and the like. Such poorly absorbed drugs can be hydrophilic, amphiphilic, or hydrophobic.

The present invention provides compositions and methods for delivering a wide variety of therapeutically and diagnostically useful molecules that are not readily absorbed through intestinal membranes. In particular, this invention relates to compounds that act as drug carriers for large and highly water soluble therapeutic molecules and to pharmaceutical ingredients comprising these carriers.

The invention works to reduce or inhibit physical and/or chemical decomposition or inactivation of active drug(s), and simultaneously increases entry of the drug into the cells and tissues, effectively increasing intestinal absorption and distribution to the blood vessels. Thereby, pharmaceutical ingredients of the invention are particularly useful for oral administration. This enhancing system is particularly useful in delivering peptide and/or protein drugs, e.g. insulin, calcitonin, and human growth hormone (HGH) or other drugs that are poorly absorbed in the gastrointestinal tract because of high water solubility or because such drug are subject to decomposition or inactivation in the conditions encountered in the gastrointestinal tract. In addition to peptide and/or protein drugs, other poorly absorbed drugs that can be effectively delivered according to the present invention include aminoglycoside antibiotics, glycopeptide antibiotics, carbapenem, and catechin, and the like.

Examples of poorly absorbed drugs that can be orally delivered according to the present invention include drugs from several categories. Protein and peptide drugs include insulin, human growth hormone, calcitonin, high density lipo-protein (HDL), erythropoietin (EPO), and the like. Aminoglycoside antibiotics include netilmicin, isepamicin, amikacin, tobramycin, gentamicin, and the like, and mixtures thereof. Glycopeptide antibiotics include teicoplanin, vancomycin, and bleomycin, and the like, and mixtures thereof. Miscellaneous drugs include daptomycin, tigecycline, ramoplanin, catechin, aztreonam, imipenem, cilastatin, and the like, and mixtures thereof. Anticancer drugs include paclitaxel and the like.

Drugs that can be delivered according to the present invention include the following. Peptide drugs include adenosine deaminase, adrenocorticotropic hormone (ACTH) and fragments thereof, angiotensin and related peptides, antibody fragments, antigens and fragments thereof, atrial natriuretic peptide, arginase, asparaginase, bioadhesive peptide, bradykinin and related peptides, calcitonin and related peptides, cell surface receptor protein fragment, chemotactic peptide, cyclosporines, chymotrypsin, cytokines, dynorphin and related peptides, endorphin and β-lidotropin fragment, enkephalin and its species peptide, enzyme inhibitors, erythropoietin, fibronectin fragment and related peptide, gastrointestinal peptide, growth hormone releasing peptide, immunostimulating peptide, interleukins, leutinizing hormone releasing hormone (LH-RH) and its related peptides, melanocyte stimulating hormone and related peptides, monoclonal antibodies (e.g., Remicade®), nuclear localization signal related peptide, neurotensin and related peptides, neurotransmitter peptide, opioid peptides, oxytocin, papain, vasopressin and related peptides, parathyroid hormone and its fragments, prolactin, protein kinase related peptide, ribonuclease, somatostatin and related peptides, substance P and its related peptides, superoxide dismutase, transforming growth factor (TGF) and related peptides, thyroid stimulating hormones, trypsin, tumor necrosis factor fragment and toxin and/or toxoid, functional peptide (angiostatin, anticancer peptide), antihypertension peptide, antibloodclotting peptide, antimicrobial peptide, and the like and mixtures thereof. Protein drugs include immunoglobulins, angiogenin, bone morphogenic protein, chemokines, colony stimulating factor (CSF) and related proteins, cytokines, growth factors, interferons, interleukins, leptin, leukemia inhibitory factor, stem cell factor, transforming growth factor, tumor necrosis factor, and the like, and mixtures thereof. Hydrophilic, amphipathic, or hydrophobic drugs that can be used according to the present invention include anti-viral agents, steroidal anti-inflammatory drugs, non-steroidal anti-inflammatory drugs, antibiotics (especially, aminoglycosides such as netilmicin, isepamicin, teicoplanin), antimicrobials, vitamins, hormones, prostaglandins, prostacyclins, anti-cancer drugs (e.g., tamoxifen), anti-metabolites, miotics, adrenaline antagonists, cholinomimetics drugs, anticonvulsants, antidepressants, antipsychotics, anaesthetics, analgesics, steroids, estrogens, lipopeptide antibiotics (e.g., daptomycin), progesterones, glycosaminoglycans, polynucleotides, immuno-suppressants, immuno-stimulators, and the like, and mixtures thereof.

Enhancers that can be used according to the present invention include sucrose fatty acid esters, such as sucrose stearate, sucrose palmitate, sucrose laurate, sucrose behenate, sucrose oleate, sucrose erucate, and the like, and mixtures thereof; phospholipid derivatives, phosphatidyl derivatives, glycosylceramides derivatives, fatty acid derivatives, nonionic surfactants, vitamin E tocopheryl succinate polyethylene glycol (TPGS) derivatives, Gelucire® series surfactants, glyceride derivatives, and the like, and mixtures thereof.

Phospholipids include phosphoglycerides. Glycerides include mono-, di-, and tri-esters of glycerol. Fatty acids are generally straight-chain carboxylic acid compounds ranging from three to 18 carbons. Fatty acids include saturated compounds, such as butyric, caproic, caprylic, capric, lauric, myristic, palmitic, and stearic acids, and unsaturated acids containing one or more double bonds per molecule. The most common of the unsaturated fatty acids are oleic acid, linoleic acid, and linolenic acid. Ceramides are N-acyl fatty acid derivatives of a sphingosine, thus, glycosylceramides are ceramides bonded to saccharide radicals.

The GELUCIRE® series of surfactants (Gattefosse S. A., Saint Priest, France) comprises glycerol esters of fatty acids. For example, GELUCIRE® 33/01 comprises glycerol esters of saturated $C_8$-$C_{18}$ fatty acids with a melting point of 33-37° C. and an HLB of 1. GELUCIRE® 39/01 comprises glycerol esters of saturated $C_{12}$-$C_{18}$ fatty acid esters with a melting point of 37.5-41.5° C. and an HLB of 1. GELUCIRE® 43/01 comprises glycerol esters of saturated $C_{12}$-$C_{18}$ saturated fatty acid esters with a melting point of 42-46° C. and an HLB of 1. GELUCIRE® 44/14 comprises a well-defined mixture of mono-, di-, and tri-glycerides and mono- and di-fatty acid esters of polyethylene glycol. It is synthesized by an alcoholysis/esterification reaction using hydrogenated palm kernel oil and PEG1500 as starting materials. The predominant fatty acid is lauric acid ($C_{12}$). It has a melting point of 42-46° C. and an HLB of 14. It is also known as lauroyl macrogol-32 glycerides. GELUCIRE® 50/13 is a well-defined mixture of mono-, di-, and tri-glycerides and mono- and di-fatty acid esters of polyethylene glycol. It is synthesized by an alcoholysis/esterification reaction using hydrogenated palm oil and PEG1500 as starting materials. The predominant fatty acid is palmitostearic acid ($C_{16}$-$C_{18}$). It has a melting point of 46-51° C. and an HLB of 13. It is also known as stearoyl macrogol-32 glycerides.

Illustrative phosphatides according to the present invention include phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), diarachidonyiphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylserine; phosphatidyl glycerols, including distearoylphosphatidylglycerol (DSPG); phosphatidylinositol; phosphatidic acids, including dipalmitoylphosphatidic acid (DPPA) and distearoylphosphatidic acid (DSPA); and the like; and mixtures thereof.

Illustrative fatty acids according to the present invention include palmitic acid, stearic acid, oleic acid, arachidonic acid, and the like, and mixtures thereof.

Illustrative nonionic surfactants according to the present invention include polyoxyethylene-polyoxypropylene glycol block copolymers, sorbitan fatty acid esters, and fluorine-containing surfactants. Illustrative of the polyoxyethylene-polyoxypropylene glycol block copolymers are α-hydroxy-ω-hydroxypoly(oxyethylene)-poly(oxypropylene)-poly(oxyethylene) block copolymers. These latter block copolymers are generally referred to as poloxamer copolymers. Examples of poloxamer copolymers that are particularly suitable for use in the present invention include, for example, poloxamer F68, poloxamer L61, and poloxamer L64. These poloxamer copolymers are commercially available from Spectrum 1100 (Houston, Tex.).

Illustrative of the sorbitan fatty acid esters are, for example, poly(oxy-1,2,-ethanediyl) derivatives of higher alkyl esters of sorbitan. Examples of such esters of sorbitan include, for example, sorbitan monolaurate, sorbitan monooleate, sorbitan monopalmitate, and sorbitan monostearate. These, as well as other derivatives of sorbitan, are typically referred to as polysorbates, including, for example, polysorbate 20, polysorbate 40, polysorbate 60, and polysorbate 80. Various of the polysorbates are commercially available from Spectrum 1100 (Houston, Tex.).

Illustrative of the fluorine-containing surfactants are surfactants containing one or more fluorine atoms. Exemplary of such surfactants include those commercially available from DuPont Chemicals (Wilmington, Del.) and sold under the trademarks ZONYL™, including, for example, ZONYL™ FSN-100 and ZONYL™ FSO-100.

Additional nonionic surfactants according to the present invention include octoxynols (e.g., TRITON-X® surfactants), polyoxyethylene sorbitans (e.g., TWEEN® surfactants), polyoxyethylene ethers (e.g., BRIJ® surfactants), polyethylene-polypropylene block copolymers (e.g., PLURONIC® surfactants), fluorosurfactants (e.g., ZONYL® surfactants), and FLUORAD® surfactants.

Promoters that can be used according to the present invention include amino acid derivatives (such as poly(amino acids)), aminosugars, and the like, and mixtures thereof. Promoters that can be used according to the present invention include glucosamine, galactosamine, N-acetylglucosamine, muramic acid, N-acetylmuramic acid, N-acetylgalactosamine, sialic acid, poly(allylamine), poly(L-lysine), poly(L-arginine), poly(L-histidine), poly(ethylenimine), poly(L/D-histidine), (poly) L-arginine, poly(ethylamine), glucagon, glycyrrhizin, glutamic acid derivatives (e.g., L-glutamine, L-glutamic acid diethyl ester), bile salts, PEG derivatives, acylcarnitines, citric acids, and the like, and mixtures thereof. Illustrative promoters that can be used according to the present invention include poly-L-lysine, glucosamine, poly-L-arginine, galactosamine, N-acetylglucosamine, and the like, and mixtures thereof.

Protectors that can be used according to the present invention include carbomers, carboxymethylcellulose, polysaccharides (kappa, iota, lambda), pectin, cellulose and derivatives thereof (such as methylcellulose and derivatives thereof, ethylcellulose and derivatives thereof, hydroxypropylcellulose and derivatives thereof), dextrin, gelatin, polyethylene oxide, poly(vinyl alcohol), poly(vinyl propylene), poly(vinylpyrrolidone) (PVP), xanthan gums, sodium alginate, methacrylic acid copolymers such as those sold under the Eudragit® trademark, colloidal silica, and synthetic silica derivatives (e.g., silicon dioxide and the like), polysaccharides, water-soluble cellulose ethers, hydroxypropylmethacrylate (RPM) acetate succinate/phthalate derivatives, tragacanth, water-soluble chitosan, polycarbophil, and the like, and derivatives thereof, and mixtures thereof. Illustrative protectors according to the present invention include methylcellulose, hydroxypropylcellulose, polyvinyl alcohol, polyvinyl pyrrolidone, and mixtures thereof.

As used herein, "PEP" means the carrier compositions according to the present invention, which include an optional protector, an enhancer, and a promoter. The carrier is mixed with a drug to result in a drug-containing composition.

The formulation is made by mixing the drug, enhancer, promoter, and optional protector to form a solution. The solution will ordinarily be dried according to methods well known in the art, such as freeze drying, spray drying, and the like, to result in a dried product. This dried product is then fabricated into a selected dosage form, such as tablets or capsules, according to well known methods. These dosage forms are coated with an enteric coating to permit the dosage forms to pass through the acidic conditions of the stomach to the intestines, wherein the coating disintegrates to permit release of the ingredients in the intestines to facilitate absorption through the intestinal mucosa and thence into the bloodstream.

As used herein, "tablets" are solid pharmaceutical dosage forms containing drug substances with or without suitable diluents and prepared either by compression or molding methods well known in the art. Tablets remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, or triangular. They may differ greatly in size and weight depending on the amount of drug substance present and the intended method of administration. They are divided into two general classes, (1) compressed tablets, and (2) molded tablets or tablet triturates. In addition to the active or therapeutic ingredient or ingredients, tablets contain a number or inert materials or additives. A first group of such additives includes those materials that help to impart satisfactory compression characteristics to the formulation, including diluents, binders, and lubricants. A second group of such additives helps to give additional desirable physical characteristics to the finished tablet, such as disintegrators, colors, flavors, and sweetening agents.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and the like.

As used herein, "binders" are agents used to impart cohesive qualities to the powdered material. Binders, or "granulators" as they are sometimes known, impart a cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like.

As used herein, "lubricants" are materials that perform a number of functions in tablet manufacture, such as improving the rate of flow of the tablet granulation, preventing adhesion of the tablet material to the surface of the dies and punches, reducing interparticle friction, and facilitating the ejection of the tablets from the die cavity. Commonly used lubricants include talc, magnesium stearate, calcium stearate, stearic acid, and hydrogenated vegetable oils.

As used herein, "disintegrators" or "disintegrants" are substances that facilitate the breakup or disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

As used herein, "coloring agents" are agents that give tablets a more pleasing appearance, and in addition help the manufacturer to control the product during its preparation and help the user to identify the product. Any of the approved certified water-soluble FD&C dyes, mixtures thereof, or their corresponding lakes may be used to color tablets. A color lake is the combination by adsorption of a water-soluble dye to a hydrous oxide of a heavy metal, resulting in an insoluble form of the dye.

As used herein, "flavoring agents" vary considerably in their chemical structure, ranging from simple esters, alcohols, and aldehydes to carbohydrates and complex volatile oils. Synthetic flavors of almost any desired type are now available.

Capsules are solid dosage forms in which the drug substance is enclosed in either a hard or soft soluble container or shell of a suitable material, such as gelatin. Encapsulation of medicinal agents remains a popular method of administering drugs, because capsules are tasteless, easily administered, and easily filled. Some patients find it easier to swallow capsules than tablets, therefore preferring to take this form when possible. This preference has prompted pharmaceutical manufacturers to mark products in capsule form even though the product has already been produced in tablet form.

Enteric coatings are films that do not permit release of a significant quantity of drug in the stomach, but which rapidly and completely release the drug when the dosage form passes into the intestine. Numerous types of enteric coatings are known in the art, such as described in Remington's Pharmaceutical Sciences.

In one illustrative embodiment of the invention, the drug is contained in one tablet or capsule, optionally together with a protector, and the enhancer and promoter are placed in another tablet or capsule. In this embodiment, the drug-containing tablet or capsule is taken together with the enhancer/promoter-containing tablet or capsule to effectuate oral administration of the drug.

The following examples are illustrative of certain aspects of the invention and are not to be considered limitations on the scope of the invention.

EXAMPLE 1

Aggregation Test

A solution of recombinant human growth hormone (rhGH) (0.5 mg/mL) was prepared in 20 mM phosphate buffer. The phosphate buffer was prepared in triple-distilled, filtered water (0.22 μm filter), and its pH was adjusted to 7.4 with sodium hydroxide solution. Solutions of rhGH were prepared fresh prior to use, and concentrations were determined by measuring UV absorbance at 278 nm. The UV absorbance at 278 nm was linearly related to concentrations in the range of 0.1 to 1 mg/mL.

The solutions of rhGH (0.5 mg/mL) were shaken for 1 min at high speed with a vortex mixer (Scientific Industries Inc.). After shaking, samples were equilibrated for 30 min at room temperature. The optical density of the resulting turbid solutions was measured at 400 nm to check the amount of insoluble aggregates. This study was conducted with and without adding a protector (e.g., polyvinyl alcohol (PVA), polyvinylpyrrolidone (PVP), and methylcellulose (MC)).

A mixture of 0.5 mg of rhGH and 1 mg of methylcellulose yielded an absorbance of 0.44 before shaking and 0.07 after shaking. A mixture of 0.5 mg of rhGH and 20 mg of PVA yielded an absorbance of 0.44 before shaking and 0.10 after shaking. A mixture of 0.5 mg of rhGH and 25 mg of PVP yielded an absorbance of 0.44 before shaking and 0.14 after shaking. Therefore, protectors can minimize aggregation by reducing the adsorption of drugs at interfaces. Thus, the use of a protector can improve the physical stability of drugs.

EXAMPLE 2

Decomposition Test

A solution of rhGH (5 ng/mL) was prepared in 20 mM phosphate buffer. The phosphate buffer was prepared in triple-distilled, filtered water (0.22 μm filter), and its pH was adjusted to pH 7.4 with sodium hydroxide solution. Solutions of rhGH were shaken for 1 min at high speed with a vortex mixer (Scientific Industries Inc.). After shaking, samples were equilibrated for specific time intervals at room temperature. Concentrations of rhGH were then determined by ELISA according to methods well known in the art. Results are presented in Table 1.

TABLE 1

| | Concentration rhGH (ng/mL) | | | | |
|---|---|---|---|---|---|
| | 0 min | 1 min | 30 min | 60 min | 90 min |
| rhGH only | 5 | 1.05 | 0.65 | 0.43 | 0.40 |
| rhGH + PC[a] | 5 | 1.30 | 0.96 | 0.68 | 0.52 |
| rhGH + GEL[b] | 5 | 1.09 | 1.00 | 0.67 | 0.61 |
| rhGH + PVP[c] | 5 | 1.10 | 0.90 | 0.82 | 0.45 |
| rhGH + PVA[d] | 5 | 1.12 | 0.69 | 0.48 | 0.48 |
| rhGH + MC[e] | 5 | 1.35 | 1.07 | 0.74 | 0.62 |
| rhGH + PC + GEL | 5 | 2.49 | 1.65 | 0.93 | 0.72 |
| rhGH + PC + PVP | 5 | 2.07 | 1.68 | 0.88 | 0.48 |
| rhGH + PC + PVA | 5 | 2.03 | 0.85 | 0.71 | 0.69 |
| rhGH + PC + MC | 5 | 3.25 | 1.78 | 1.02 | 1.10 |

[a]glucosamine and sucrose laurate 16
[b]Gelucire ® 44/14
[c]polyvinylpyrrolidone
[d]polyvinyl alcohol
[e]methylcellulose These results show that the present invention reduces decomposition of a drug.

EXAMPLE 3

RhGH solutions containing a promoter (glucosamine or poly-L-lysine), an enhancer (sucrose laurate 16), and a protector (methylcellulose) were prepared in water according to the proportions set out in Table 2.

TABLE 2

| | PEP1 | PEP2 |
|---|---|---|
| rhGH | 3 mg/kg | 3 mg/kg |
| glucosamine | 1.2 mg/kg | — |
| sucrose laurate 16 | 40 mg/kg | 400 mg/kg |
| poly(L-lysine) | — | 12 mg/kg |
| methylcellulose | 6 mg/kg | 6 mg/kg |

To determine absorption from the intestine, male Sprague-Dawley rats with free access to water were fasted for approximately 12 h. On the day of experiment, these rats were anesthetized and shaved on the abdomen. A 2-cm midline incision was made through the muscle and the stomach was externalized with rounded forceps. A small incision was made in the forestomach region, where the blood supply was sparse, to insert a polyethylene tube toward the middle duodenum, which was closed at the exposed end by a stopcock to prevent drainage of drug solution from the duodenum. This tube was guided through the stomach and the pyloric sphincter into the duodenum, about 5 cm past the sphincter, and was fixed at the stomach. The abdominal muscle was sutured under the skin. At specific time intervals, blood was taken from each rat and centrifuged. Four rats were in each treatment group. About 50 μg of serum was analyzed by ELISA test kit and the concentration of rhGH was calculated. The results are represented in Table 3. In the case of rhGH administered without PEP solution, rhGH was not detected.

TABLE 3

| | Average plasma concentration rhGH (ng/mL) | |
|---|---|---|
| Time (min) | PEP1 | PEP2 |
| 10 | 197.21 | 253.28 |
| 20 | 155.15 | 276.04 |

TABLE 3-continued

| | Average plasma concentration rhGH (ng/mL) | |
|---|---|---|
| Time (min) | PEP1 | PEP2 |
| 40 | 39.26 | 292.21 |
| 60 | 33.82 | 302.32 |
| 75 | 3.38 | 376.47 |
| 90 | 0 | 339.98 |

EXAMPLE 4

To determine absorption from the intestine, male Sprague Dawley rats weighing 250-300 g with free access to water were fasted for about 18 h prior to experiments. These rats were anesthetized and maintained with Ketamine/Xylazine ((60 gm/kg)/(80 mg/kg)) by intraperitoneal injection. The small intestine was exposed by a midline abdominal incision. A small incision was made in the stomach to insert a polyethylene tube (i.d. 0.76 mm, o.d. 1.22 mm, Clay Adams), toward the middle duodenum, which was closed at the exposed end by a stopcock to prevent drainage of drug solution from the duodenum. Blood samples were taken with a heparinized syringe through the jugular vein catheter at predetermined time intervals. After collecting, samples were coagulated for about 90 min and then were centrifuged for 10 min at 6000 rpm. The supernatant was removed and stored at −20° C. Samples were analyzed for hGH protein levels with a Human Growth Hormone ELISA Kit (coated plate, ICN Diagnostics) according to the manufacturer's protocol.

Figure 2:
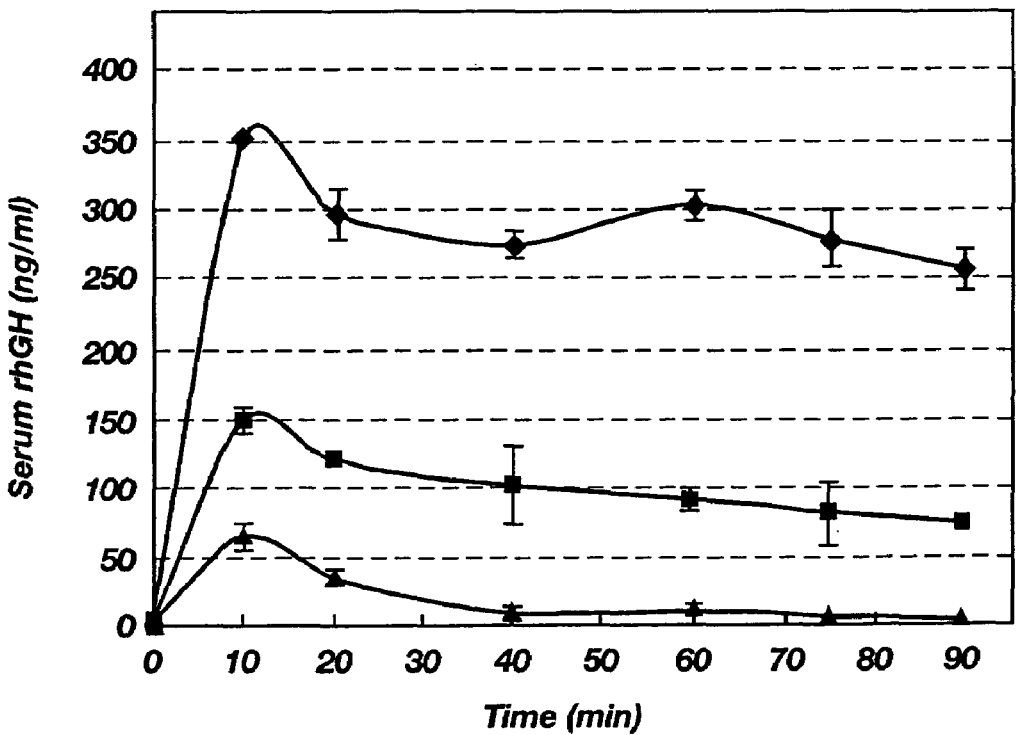
FIG. 2 shows serum rhGH concentration over time after intraduodenal administration with 1 mg/kg rhGH (▲), 3 mg/kg rhGH (■), or 10 mg/kg rhGH (♦) and a fixed amount of carrier (10 units); n=3-4 rats.

For the controls, either glucosamine 40 mg/kg plus sucrose laurate 40 mg/kg (i.e., 100 units of carrier) or 10 mg/kg of rhGH (Advanced Protein Technologies Inc., Suwon, Korea) were administered per intraduodenum. Subcutaneous dosing was 0.1 mg/kg rhGH, which showed a peak serum rhGH concentration of 73 ng/ML with a Tmax of 40 min. To evaluate the effect of varying the amount of carrier administered, the amount of rhGH was held at 3 mg/kg rhGH and the Tmax was measured. The Tmax was less than 20 min for all doses, which showed that absorption of rhGH was not proportional to the carrier dose. However, the data demonstrated a relationship between the rhGH dose administered and the plasma concentration of rhGH at a fixed carrier dose of 10 units. In the case of subcutaneous administration (FIG. 1), the serum plasma concentration profile was shown to be dose dependent. In the case of intraduodenal administration, the controls were fixed at 10 units of carrier. The amount of rhGH was varied to include 1, 3, and 10 mg/kg of rhGH. As with the intraduodenal study, the differences of concentration were dose dependent (FIG. 2). As for bioavailability, 3 mg/kg of rhGH showed 7.1% (10 units dose carrier) and 10 mg/kg rhGH showed 6.1% (10 units dose carrier).

Figure 3:
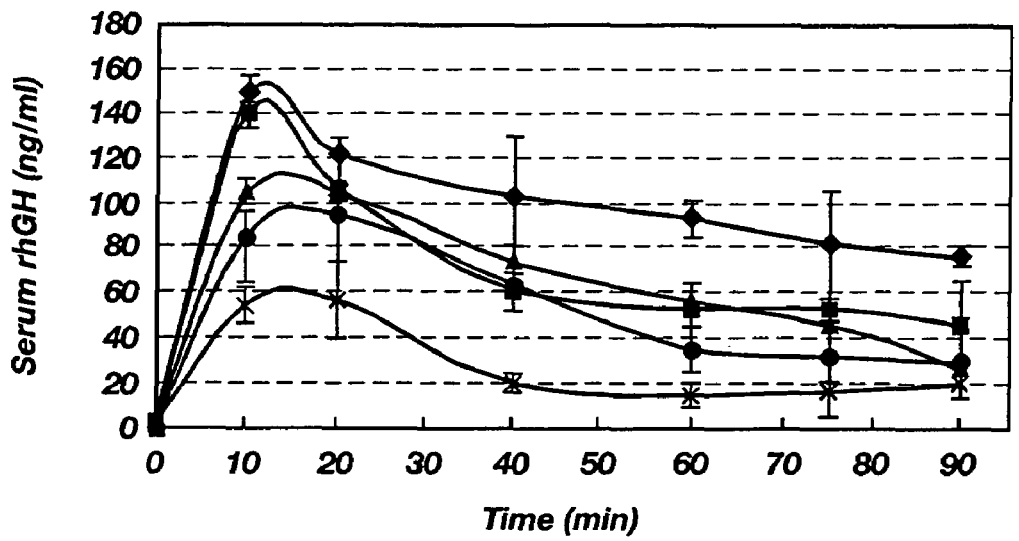
FIG. 3 shows serum rhGH concentration over time after intraduodenal administration of 3 mg/kg of rhGH with 5 units (X), 10 units (●), 20 units (▲), 50 units (■), or 100 units (♦) of carrier; n=3-4 rats.
Figure 4:
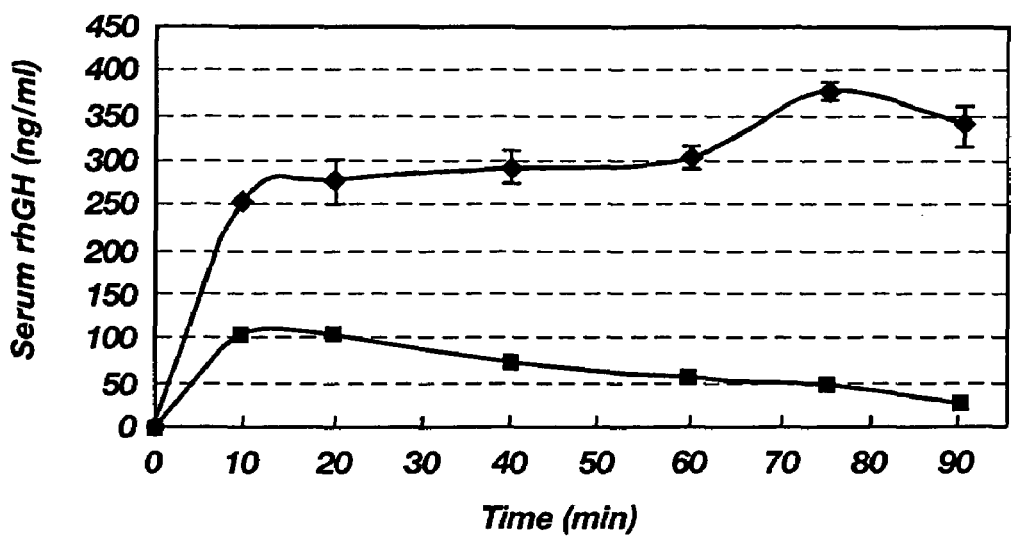
FIG. 4 shows serum rhGH concentration over time after intraduodenal administration of 3 mg/kg rhGH with a poly (L-lysine)/sucrose laurate 16 carrier (♦) or glucosamine/sucrose laurate 16 carrier (■).

This experiment demonstrated that the rhGH levels were dose dependent when the carrier amount was fixed (FIG. 2). When rhGH was fixed at 3 mg/kg and the amount of carrier was varied at 100, 50, 20, 10, and 5 units, the results showed that small amounts of the carrier (10-20 units) exhibited increased absorption of rhGH compared to higher dosages of carrier (FIG. 3). Finally, to evaluate the effectiveness of the carrier itself, the type of carrier was varied while maintaining the same level of rhGH (3 mg/kg). The carrier containing poly(L-lysine and sucrose laurate 16 showed increased absorption compared to the carrier containing glucosamine and sucrose laurate 16 (FIG. 4) based on the calculated availabilities of 21.3% and 6.6%, respectively.

Thus, the carrier system of the present invention significantly improved intraduodenal absorption of rhGH without modification of the drug. The carrier system is effective for oral delivery of rhGH based on therapeutic levels of the drug.

EXAMPLE 5

Figure 5:
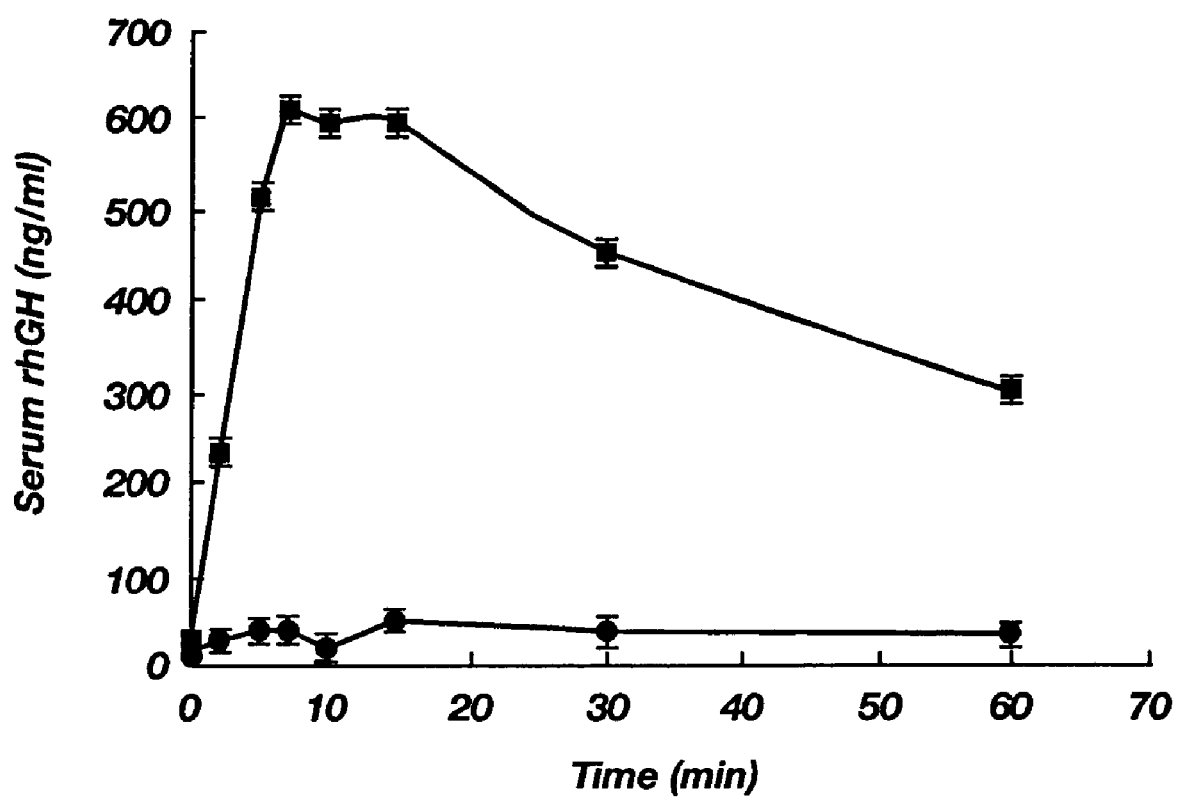
FIG. 5 shows serum insulin concentration over time after intraduodenal administration of insulin to diabetes induced rats: insulin control, 2 IU/kg (●); insulin (50 IU/kg)/carrier (100 units) (■); n=2.
Figure 6:
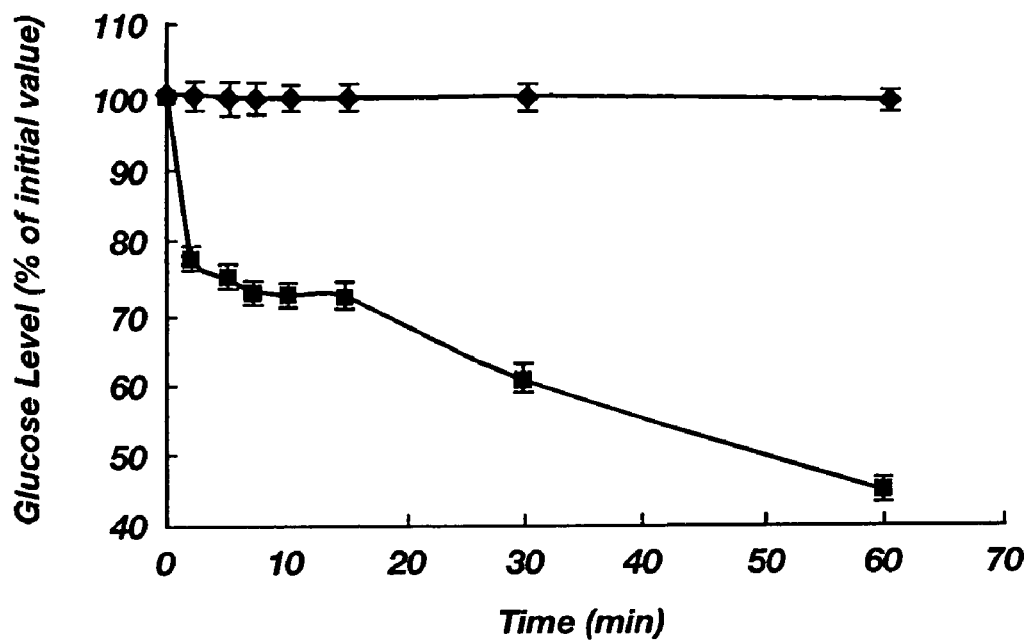
FIG. 6 shows serum glucose levels over time after intraduodenal administration of insulin (with zinc) to diabetes induced rats: insulin control, 2 IU/kg (♦); insulin (50 IU/kg)/carrier (100 units) (■); n=2.
Figure 7:
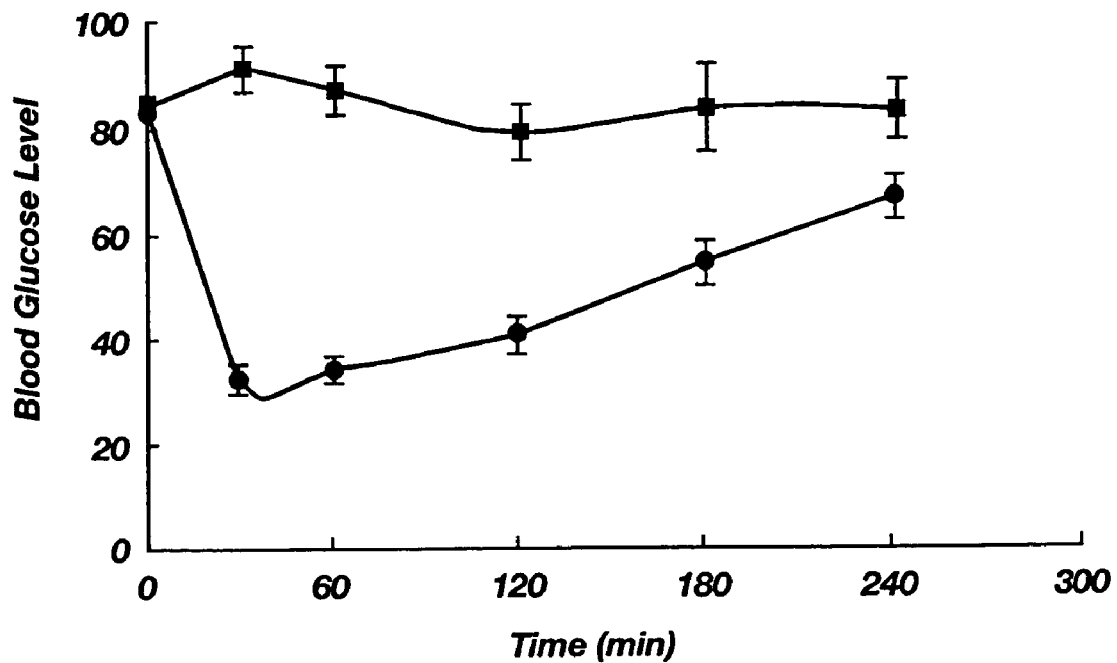
FIG. 7 shows serum glucose levels over time after intraduodenal administration of insulin to non-diabetic rats: insulin control, 2 IU/kg (subcutaneous, n=3) (●); insulin (50 IU/kg)/carrier (100 units) (I.D., n=5) (■).

Insulin was dissolved in 0.01 N HCl and was then mixed with a protector (methylcellulose), an enhancer (sucrose laurate 16), and a promoter (glucosamine) in water before administration to rats. The insulin/PEP solutions were mixed by magnetic stirrer at room temperature. The composition of the insulin/PEP solution was formulated such that an individual dosage contained 50 IU/kg of insulin, 400 mg/kg of sucrose laurate 16, glucosamine in a weight ratio of 1:4 of insulin to glucosamine, and methylcellulose in a weight ratio of 1:0.5 of insulin to methylcellulose. The insulin/PEP composition was administered to rats according to the procedure of Example 3. At specific time intervals, blood was taken from each rat and centrifuged. Plasma was analyzed by glucose meter and radioimmunoassay test kit (ICN pharmaceuticals) for determining blood glucose and insulin concentrations. The results are presented in FIGS. 5-7.

In diabetic rats, serum insulin was detected in the blood (FIG. 5) and significant hypoglycemic effects were observed (FIG. 6) following administration of insulin in the carrier of the present invention. No significant hypoglycemic response was registered in non-diabetic rats (FIG. 7) following similar treatment. Autoregulation of insulin secretion and the secretion of counter-regulatory hormones may have offset the activity of the exogenously supplied insulin in these non-diabetic rats.

Thus, the carrier of the present invention significantly improved intraduodenal absorption of insulin without modification of the drug.

EXAMPLE 6

Calcitonin was dissolved in water and was then mixed with a protector (methylcellulose), an enhancer (sucrose laurate 16), and a promoter (glucosamine) in water before administration to rats. The insulin/PEP solutions were mixed by magnetic stirrer at room temperature. The composition of the calcitonin/PEP solution was formulated such that an individual dosage contained 2 mg/kg of calcitonin, 40 mg/kg of sucrose laurate 16, glucosamine in a weight ratio of 1:4 of calcitonin to glucosamine, and methylcellulose in a weight ratio of 1:0.5 of calcitonin to methylcellulose. The calcitonin/PEP composition was administered to rats according to the procedure of Example 3. At specific time intervals, blood was taken from each rat and centrifuged. Plasma was analyzed by ELISA according to methods well known in the art. The results are presented in Table 4.

TABLE 4

| Time (min) | Average plasma concentration of Calcitonin (ng/mL) |
| --- | --- |
| 15 | 8.02 |
| 30 | 8.61 |
| 45 | 10.95 |
| 60 | 7.55 |
| 90 | 3.36 |
| 120 | 1.72 |
| 180 | 0.69 |
| 240 | 0.99 |

EXAMPLE 7

Isepamicin solution was mixed with methylcellulose solution, and the resulting mixture was mixed with solutions of glucosamine and sucrose stearate 16 in water before administration to rats. The isepamicin and PEP solutions were mixed by magnetic stirrer at room temperature, forming an isepamicin-PEP solution. The contents of isepamicin/PEP comprised an individual dosage of 75 mg/kg isepamicin, 400 mg/kg sucrose stearate, glucosamine in a 1:4 mole ratio of isepamicin to glucosamine, and methylcellulose in a 1:0.5 mole ratio of isepamicin to methylcellulose. The isepamicin/PEP composition was administered to rats according to the procedure of Example 3. At specific time intervals, blood was taken from each rat and centrifuged. Plasma was analyzed by HPLC, and bioavailability was calculated. The results were represented in Table 5.

TABLE 5

| Time (min) | Average Plasma Concentration of Isepamicin (µg/mL) |
| --- | --- |
| 30 | 84.24 |
| 60 | 101.78 |
| 120 | 73.63 |
| 180 | 49.87 |
| 240 | 43.90 |
| 360 | 35.75 |

EXAMPLE 8

Netilmicin solution was mixed with a solution of methylcellulose, and this mixture was added to solutions of glucosamine and sucrose stearate in water before administration to rats. The netilmicin and PEP solutions were mixed by magnetic stirrer at room temperature, forming a netilmicin-PEP solution. The contents of netilmicin/PEP comprised an individual dosage of 80 mg/kg netilmicin, 400 mg/kg sucrose stearate, glucosamine in a 1:4 mole ratio of netilmicin to glucosamine, and methylcellulose in a 1:0.5 mole ratio of netilmicin to methylcellulose. The netilmicin/PEP composition was administered to rats according to the procedure of Example 3. At specific time intervals, blood was taken from each rat and centrifuged. Plasma was analyzed by HPLC, and bioavailability was calculated. The results are represented in Table 6.

TABLE 6

| Time (min) | Average plasma concentration Netilmicin (µg/mL) |
| --- | --- |
| 30 | 62.07 |
| 60 | 70.74 |
| 120 | 39.28 |
| 180 | 38.88 |
| 240 | 35.75 |
| 360 | 34.79 |

These results show that the percent bioavailability was 73.05%.

EXAMPLE 9

Teicoplanin solution was mixed with a solution of methylcellulose, and this mixture was added to solutions of glucosamine and sucrose stearate in water before administration to rats. The teicoplanin and PEP solutions were mixed by magnetic stirrer at room temperature, forming a teicoplanin/PEP solution. The contents of teicoplanin/PEP comprised an individual dosage of 64 mg/kg teicoplanin, 400 mg/kg sucrose stearate, glucosamine in a 1:4 mole ratio of teicoplanin to glucosamine, and methylcellulose in a 1:0.5 mole ratio of teicoplanin to methylcellulose. The teicoplanin/PEP composition was administered to rats according to the procedure of Example 3. At specific time intervals, blood was taken from each rat and centrifuged. Plasma was analyzed by HPLC, and bioavailability was calculated. The results are represented in Table 7.

TABLE 7

| Time (min) | Average plasma concentration Teicoplanin (µg/mL) |
|---|---|
| 30 | 11.14 |
| 60 | 9.50 |
| 120 | 10.36 |
| 180 | 12.22 |
| 240 | 11.29 |

These results show a percent bioavailability of 35.07%.

EXAMPLE 10

Catechin solution was mixed with a solution of methylcellulose, and this mixture was added to solutions of glucosamine and sucrose palmitate in water before administration to rats. The catechin and PEP solutions were mixed by magnetic stirrer at room temperature, forming a catechin/PEP solution. The contents of catechin/PEP comprised and individual dosage of 300 mg/kg catechin, 400 mg/kg sucrose palmitate, glucosamine in a 1:4 mole ratio of catechin to glucosamine, and methylcellulose in a 1:0.5 mole ratio of catechin to methylcellulose. The catechin/PEP composition was administered to rats according to the procedure of Example 3. At specific time intervals, blood was taken from each rat and centrifuged. Plasma was analyzed by HPLC, and bioavailability was calculated. The results are represented in Table 8.

TABLE 8

| | Concentration (µg/mL) | |
|---|---|---|
| Time (min) | Catechin control | Catechin/PEP |
| 0 | 1.17 | 0.47 |
| 15 | 4.48 | 43.66 |
| 30 | 7.83 | 57.04 |
| 60 | 10.72 | 65.94 |
| 90 | 14.6 | 62.28 |
| 120 | 17.53 | 50.99 |
| 180 | 18.74 | 32.16 |

EXAMPLE 11

Aztreonam solution (containing arginine as a pH adjuster) was mixed with a solution of methylcellulose, and this mixture was added to solutions of glucosamine and sucrose palmitate in water before administration to rats. The aztreonam and PEP solutions were mixed by magnetic stirrer at room temperature, forming an Aztreonam-PEP solution. The contents of aztreonam/PEP comprised an individual dosage of 40 mg/kg aztreonam, 400 mg/kg sucrose palmitate, glucosamine in a 1:4 mole ratio of aztreonam to glucosamine, methylcellulose in a 1:0.5 mole ratio of aztreonam to methylcellulose, and arginine in a 1:0.6 mole ratio of aztreonam to arginine. The aztreonam/PEP composition was administered to rats according to the procedure of Example 3. At specific time intervals, blood was taken from each rat and centrifuged. Plasma was analyzed by HPLC, and bioavailability was calculated. The results are represented in Table 9.

TABLE 9

| Time (min) | Average plasma concentration Aztreonam (µg/mL) |
|---|---|
| 30 | 95.38 |
| 60 | 96.99 |
| 90 | 87.88 |
| 120 | 89.57 |
| 180 | 66.99 |
| 240 | 55.24 |

These results show a percent bioavailability of 91.1±14.6%.

EXAMPLE 12

Paclitaxel solution was prepared by adding Solutol or TPGS (solubilizer), which was then mixed with a solution of methylcellulose, and this mixture was added to solutions of glucosamine and sucrose palmitate in water before administration to rats. The paclitaxel and PEP solutions were mixed by magnetic stirrer at room temperature, forming paclitaxel/PEP solutions. The contents of paclitaxel/PEP solutions are set out in Table 10.

TABLE 10

| | PEP10 | PEP11 |
|---|---|---|
| Paclitaxel | 20 mg/kg | 20 mg/kg |
| Solutol | TXL 10 mg/ml | |
| TPGS | | TXL 10 mg/ml |
| glucosamine | 10 mg/kg | 20 mg/kg |
| methylcellulose$^a$ | — | — |
| sucrose stearate 16 | 200 mg/kg | 400 mg/kg |

$^a$Paclitaxel:methylcellulose mole ratio = 1:0.5

The paclitaxel/PEP compositions were administered to rats according to the procedure of Example 3. At specific time intervals, blood was taken from each rat and centrifuged. Plasma was analyzed by HPLC, and bioavailability was calculated. The results are represented in Table 11.

TABLE 11

| | Paclitaxel Concentration (µg/mL) | |
|---|---|---|
| Time (min) | PEP10 | PEP11 |
| 5 | 2.43 | 1.82 |
| 15 | 1.89 | 1.95 |
| 30 | 1.80 | 3.49 |
| 60 | 1.50 | 3.88 |
| 90 | 2.47 | 3.29 |
| 120 | 4.46 | 4.14 |
| 180 | 3.98 | 0.61 |

The bioavailability of PEP10 and PEP11, respectively, were 20.7% and 21.3%.

The subject matter claimed is:

1. A composition for oral delivery of a pharmaceutical agent that is poorly absorbed through the intestinal mucosa, the composition comprising a mixture of an effective amount of the pharmaceutical agent; an enhancer for increasing absorption of the pharmaceutical agent through the intestinal mucosa; a promoter that functions synergistically with the enhancer for further increasing absorption of the pharmaceutical agent through the intestinal mucosa; and a protector for inhibiting decomposition or inactivation of the pharmaceutical agent;
   wherein the enhancer is a fatty acid ester selected from the group consisting of sucrose stearate, sucrose palmitate, sucrose laurate, sucrose behenate, sucrose oleate, sucrose erucate, and mixtures thereof;
   wherein the promoter is a member selected from the group consisting of amino acid derivatives, aminosugars, and mixtures thereof; and
   wherein the protector is a member selected from the group consisting of carbomers, carboxymethylcellulose, polysaccharides, pectin, cellulose, dextrin, gelatin, polyethylene oxide, poly(vinyl alcohol), poly(vinyl propylene), poly(vinylpyrrolidone), xanthan gums, sodium alginate, methacrylic acid copolymers, colloidal silica, synthetic silica, water-soluble cellulose ethers, hydroxypropylmethacrylates, tragacanth, water-soluble chitosan, polycarbophil, derivatives thereof, and mixtures thereof.

2. The composition of claim 1 wherein the protector is a member selected from the group consisting of methylcellulose, hydroxypropylcellulose, polyvinyl alcohol, polyvinyl pyrrolidone, and mixtures thereof.

3. The composition of claim 1 wherein the promoter is a member selected from the group consisting of glucosamine, galactosamine, N-acetylglucosamine, muramic acid, N-acetylmuramic acid, N-acetylgalactosamine, sialic acid, poly(allylamine), poly(L-lysine), poly(L-arginine), poly(L-histidine), poly(ethylenimine), poly(L/D-histidine), poly(L-arginine), poly(allylamine), poly(ethylamine), glucagon, glycyrrhizin, glutamic acid derivatives, bile salts, poly(ethylene glycol) derivatives, acylcarnitines, citric acids, and mixtures thereof.

4. The composition of claim 3 wherein the promoter is a member selected from the group consisting of poly-L-lysine, glucosamine, poly-L-arginine, galactosamine, N-acetylglucosamine, and mixtures thereof.

5. The composition of claim 1 wherein the pharmaceutical agent comprises a peptide or protein.

6. The composition of claim 1 wherein the pharmaceutical agent comprises insulin.

7. A composition for oral delivery of a pharmaceutical agent that is poorly absorbed through the intestinal mucosa after oral administration, the composition comprising a mixture of an effective amount of the pharmaceutical agent; an enhancer for increasing absorption of the pharmaceutical agent through the intestinal mucosa wherein the enhancer comprises a sucrose fatty acid ester selected from the group consisting of sucrose stearate, sucrose palmitate, sucrose laurate, sucrose behenate, sucrose oleate, sucrose erucate, and mixtures thereof; a promoter that functions synergistically with the enhancer for increasing absorption of the pharmaceutical agent through the intestinal mucosa when wherein the promoter comprises glucosamine or poly(L-lysine); and a protector for inhibiting decomposition or inactivation of the pharmaceutical agent wherein the protector comprises methylcellulose or poly(vinyl alcohol).

8. The composition of claim 7 wherein the sucrose fatty acid ester comprises sucrose stearate.

9. The composition of claim 7 wherein the sucrose fatty acid ester comprises sucrose palmitate.

10. The composition of claim 7 wherein the promoter comprises glucosamine.

11. The composition of claim 7 wherein the protector comprises methylcellulose.

12. A composition for oral delivery of a hydrophilic or amphipathic drug, the composition comprising a mixture of the drug and an enhancer for increasing absorption of the drug through the intestinal mucosa, wherein the enhancer is a fatty acid ester selected from the group consisting of sucrose stearate, sucrose palmitate, sucrose laurate, sucrose behenate, sucrose oleate, sucrose erucate, and mixtures thereof; a promoter for functioning synergistically with the enhancer for further increasing absorption of the drug through the intestinal mucosa, wherein the promoter comprises an aminosugar; and a protector for inhibiting decomposition or inactivation of the pharmaceutical agent.

13. The composition of claim 12 wherein the enhancer is a glycerol ester of a fatty acid.

14. The composition of claim 12 wherein the protector is a member selected from the group consisting of carbomers, carboxymethylcellulose, polysaccharides, pectin, cellulose, dextrin, gelatin, polyethylene oxide, poly(vinyl alcohol), poly(vinyl propylene), poly(vinylpyrrolidone), xanthan gums, sodium alginate, methacrylic acid copolymers, colloidal silica, synthetic silica, water-soluble cellulose ethers, hydroxypropyl methacrylates, tragacanth, water-soluble chitosan, polycarbophil, derivatives thereof, and mixtures thereof.

15. The composition of claim 12 wherein the promoter comprises glucosamine.

16. A dosage form for oral delivery of a drug that is poorly absorbable in the intestine, the dosage form comprising
   an effective amount of the drug;
   an enhancer for increasing absorption of the drug through the intestinal mucosa, wherein the enhancer comprises a sucrose fatty acid ester selected from the group consisting of sucrose stearate, sucrose palmitate, sucrose laurate, sucrose behenate, sucrose oleate, sucrose erucate, and mixtures thereof;
   a promoter for functioning synergistically with the enhancer for further increasing absorption of the drug through the intestinal mucosa; and
   a protector for reducing or inhibiting decomposition or inactivation of the drug in the gastrointestinal tract.

17. The dosage form of claim 16 wherein the dosage form comprises a tablet.

18. The dosage form of claim 17 wherein the tablet further comprises a member selected from the group consisting of diluents, binders, lubricants, disintegrators, colors, flavors, sweetening agents, and mixtures thereof.

19. The dosage form of claim 17 wherein the dosage form comprises a capsule.

20. The dosage form of claim 16 further comprising an enteric coating.

21. A method for increasing intestinal absorption of a poorly absorbable drug, the method comprising orally administering a composition comprising a mixture of the drug;

an enhancer for increasing absorption of the drug through the intestinal mucosa, wherein the enhancer comprises a sucrose fatty acid ester selected from the group consisting of sucrose stearate, sucrose palmitate, sucrose laurate, sucrose behenate, sucrose oleate, sucrose erucate, and mixtures thereof;

a promoter that functions synergistically with the enhancer for further increasing absorption of the drug through the intestinal mucosa; and a protector for reducing or inhibiting decomposition or inactivation of the drug in the gastrointestinal tract.

* * * * *